United States Patent
Inada

(10) Patent No.: US 9,770,162 B2
(45) Date of Patent: Sep. 26, 2017

(54) WIRE-PULLING MECHANISM AND ENDOSCOPIC APPARATUS

(71) Applicant: OLYMPUS CORPORATION, Shibuya-ku, Tokyo (JP)

(72) Inventor: Ayumu Inada, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 525 days.

(21) Appl. No.: 14/167,419

(22) Filed: Jan. 29, 2014

(65) Prior Publication Data

US 2014/0148646 A1 May 29, 2014

Related U.S. Application Data

(63) Continuation of application No. PCT/JP2012/069866, filed on Aug. 3, 2012.

(30) Foreign Application Priority Data

Aug. 3, 2011 (JP) ................................. 2011-170053

(51) Int. Cl.
*A61B 1/00* (2006.01)
*A61B 1/01* (2006.01)
(Continued)

(52) U.S. Cl.
CPC .............. *A61B 1/01* (2013.01); *A61B 1/0052* (2013.01); *A61B 1/0057* (2013.01); *G05G 9/047* (2013.01); *A61B 1/00052* (2013.01)

(58) Field of Classification Search
CPC ................................................ G02B 23/2476
(Continued)

(56) References Cited

U.S. PATENT DOCUMENTS 4,919,112 A * 4/1990 Siegmund .......... A61B 1/00105
600/136
2007/0221701 A1* 9/2007 Ortiz .................... A61B 17/068
227/175.1

(Continued)

FOREIGN PATENT DOCUMENTS

EP       1886617 A1    2/2008
JP       49-26677 B1   7/1974
(Continued)

OTHER PUBLICATIONS

International Search Report (ISR) dated Sep. 11, 2012 (and English translation thereof) issued in International Application No. PCT/JP2012/069866.

(Continued)

*Primary Examiner* — Alexandra Newton
(74) *Attorney, Agent, or Firm* — Holtz, Holtz & Volek PC

(57) ABSTRACT

In a wire-pulling mechanism, a second engaging portion is configured so that the position of the second engaging portion in the longitudinal direction of a second pulling wire is displaceable closer to the front end than an engaged portion of the second pulling wire, the second pulling wire is configured so as to enter the inside of a second movement track and extend in the shape of a straight line, in a neutral state of an operating unit, and the tilting operation of the operating unit causes the second engaging portion to be moved to the front end along the second movement track with respect to the second pulling wire and causes the engaged portion of the second pulling wire and the second engaging portion to be separated from each other from a state where the engaged portion of the second pulling wire and the second engaging portion engage each other.

17 Claims, 12 Drawing Sheets

(51) Int. Cl.
  *G05G 9/047* (2006.01)
  *A61B 1/005* (2006.01)

(58) Field of Classification Search
  USPC .......................................................... 600/146
  See application file for complete search history.

(56) References Cited

U.S. PATENT DOCUMENTS

2009/0209820 A1   8/2009   Tanaka
2010/0160730 A1   6/2010   Konomura

FOREIGN PATENT DOCUMENTS

| | | |
|---|---|---|
| JP | 2003-325437 A | 11/2003 |
| JP | 2004-321492 A | 11/2004 |
| JP | 2009-089955 A | 4/2009 |
| JP | 4658536 B2 | 3/2011 |
| JP | 2011-067381 A | 4/2011 |
| WO | WO 2006/126265 A1 | 11/2006 |

OTHER PUBLICATIONS

Extended European Search Report dated May 13, 2015, issued in counterpart European Application No. 12819227.5.

\* cited by examiner

WIRE-PULLING MECHANISM AND ENDOSCOPIC APPARATUS

This application is a continuation application based on PCT/JP2012/069866, filed on Aug. 3, 2012, claiming priority based on Japanese Patent Application No. 2011-170053, filed in Japan on Aug. 3, 2011. The contents of both the Japanese Patent Application and the PCT Application are incorporated herein by reference.

TECHNICAL FIELD

The present invention relates to a wire-pulling mechanism and an endoscopic apparatus.

BACKGROUND ART

In the related art, endoscopic apparatuses are known that allow an observation of places where an observer does not have a direct view, such as an inside of an object to be observed.

For example, Japanese Unexamined Patent Application, First Publication No. 2009-89955 discloses an endoscopic apparatus having an imaging mechanism provided at the distal of a pipe serving as an insertion section, an operating unit provided at a proximal end portion of the pipe and operated by a user, a plurality of pulling wires that are inserted through the inside of the pipe and has one end connected to the imaging mechanism and the other end connected to the operating unit, and a bearing mechanism that supports the operating unit so as to be rotatable in three dimensions around a rocking point.

In this endoscopic apparatus, the orientation of the imaging mechanism can be freely changed by operating the operating unit to adjust the pulling state and loosing state of the plurality of pulling wires.

SUMMARY OF THE INVENTION

Solution to Problem

A wire-pulling mechanism according to a first aspect of the present invention includes a first pulling wire and a second pulling wire each having one end connected to a body to be operated provided at a front end and having an engaged portion at the other end extending rearward from the one end; an operating unit for pulling the first pulling wire or the second pulling wire through a tilting operation of a user; and a pulling arm having a first engaging portion that is engageable with or separable from the engaged portion of the first pulling wire and a second engaging portion that is engageable with or separable from the engaged portion of the second pulling wire, the first engaging portion pulling the first pulling wire along a first movement track when the first engaging portion moves rearward in a state where the first engaging portion and the engaged portion of the first pulling wire engage each other, and the second engaging portion moving along a second movement track when the second engaging portion moves to the front end, the pulling of the first engaging portion and the moving of the second engaging portion are caused by a turning motion accompanying the tilting operation of the operating unit. The second engaging portion is configured so that a position of the second engaging portion in a longitudinal direction of the second pulling wire is capable of being displaced closer to the front end than the engaged portion of the second pulling wire. The second pulling wire is configured so as to enter an inside of the second movement track and extend in a straight line, in a neutral state of the operating unit. In a state where the engaged portion of the second pulling wire and the second engaging portion engage each other, the tilting operation of the operating unit causes the second engaging portion to be moved to the front end along the second movement track with respect to the second pulling wire and causes the engaged portion of the second pulling wire and the second engaging portion to be separated from each other.

According to a second aspect of the present invention, in the first aspect, the second engaging portion may have a wire insertion region that is movable relative to the second pulling wire, and the engaged portion that is provided at the second pulling wire may be a regulating member of which an outer shape is formed so as to be larger than the wire insertion region.

According to a third aspect of the present invention, in the second aspect, the first engaging portion and the second engaging portion may be a receiving member formed with a circular tapered hole having a taper of which a diameter increases gradually toward a front, the receiving member is formed in the wire insertion region, a shape of the regulating member may be a substantially spherical shape of which a diameter is larger than a minimum internal diameter of the tapered hole of the receiving member, and the regulating member may come into contact with a tapered surface of the tapered hole in the neutral state.

According to a fourth aspect of the present invention, in the first aspect, the engaged portion of the second pulling wire may have an engaging portion insertion region where the second engaging portion is movable in an extending direction of the second pulling wire relative to the second pulling wire, and the second engaging portion may be a contacting member that comes into contact with a rear end portion of the engaging portion insertion region.

According to a fifth aspect of the present invention, in the fourth aspect, the engaging portion insertion region may be an elongated hole that is formed toward the longitudinal direction of the second pulling wire, the engaged portion of the second pulling wire may be a connecting member having the elongated hole, and the contacting member may be inserted through the elongated hole of the connecting member and may be provided so as to be movable along the elongated hole.

According to a sixth aspect of the present invention, in any one of the first aspect to fifth aspect, an auxiliary pulling member made of an elastic body may be installed on the other end side of the second pulling wire, a front end side of the auxiliary pulling member is coupled to the other end side of the second pulling wire, a rear end side of the auxiliary pulling member may be supported by a predetermined supporting member, and the auxiliary pulling member may bias the second pulling wire rearward.

An endoscopic apparatus according to a seventh aspect of the present invention includes a first pulling wire and a second pulling wire each having one end connected to a distal side of an insertion section, having the other end arrange within an operating section, and having an engaged portion at the other end; an operating unit for pulling the first pulling wire or the second pulling wire through a tilting operation of a user; and a pulling arm having a first engaging portion that is engageable with or separable from the engaged portion of the first pulling wire and a second engaging portion that is engageable with or separable from the engaged portion of the second pulling wire, the first engaging portion pulling the first pulling wire along a first movement track when the first engaging portion moves rearward in a state where the first engaging portion and the engaged portion of the first pulling wire engage each other, and the second engaging portion moving along a second movement track when the second engaging portion moves to a front end, the pulling of the first engaging portion and the moving of the second engaging portion are caused by a turning motion accompanying the tilting operation of the operating unit. The second engaging portion is configured so that a position of the second engaging portion in a longitudinal direction of the second pulling wire is capable of being displaced closer to the front end than the engaged portion of the second pulling wire. The second pulling wire is configured so as to enter an inside of the second movement track and extend in a shape of a straight line, in a neutral state of the operating unit. In a state where the engaged portion of the second pulling wire and the second engaging portion engage each other, the tilting operation of the operating unit causes the second engaging portion to be moved to the front end along the second movement track with respect to the second pulling wire and the engaged portion of the second pulling wire and the second engaging portion to be separated from each other.

DESCRIPTION OF EMBODIMENTS

First Embodiment

A wire-pulling mechanism and an endoscopic apparatus of a first embodiment of the present invention will be described with reference to FIGS. 1 to 8.

Figure 1:
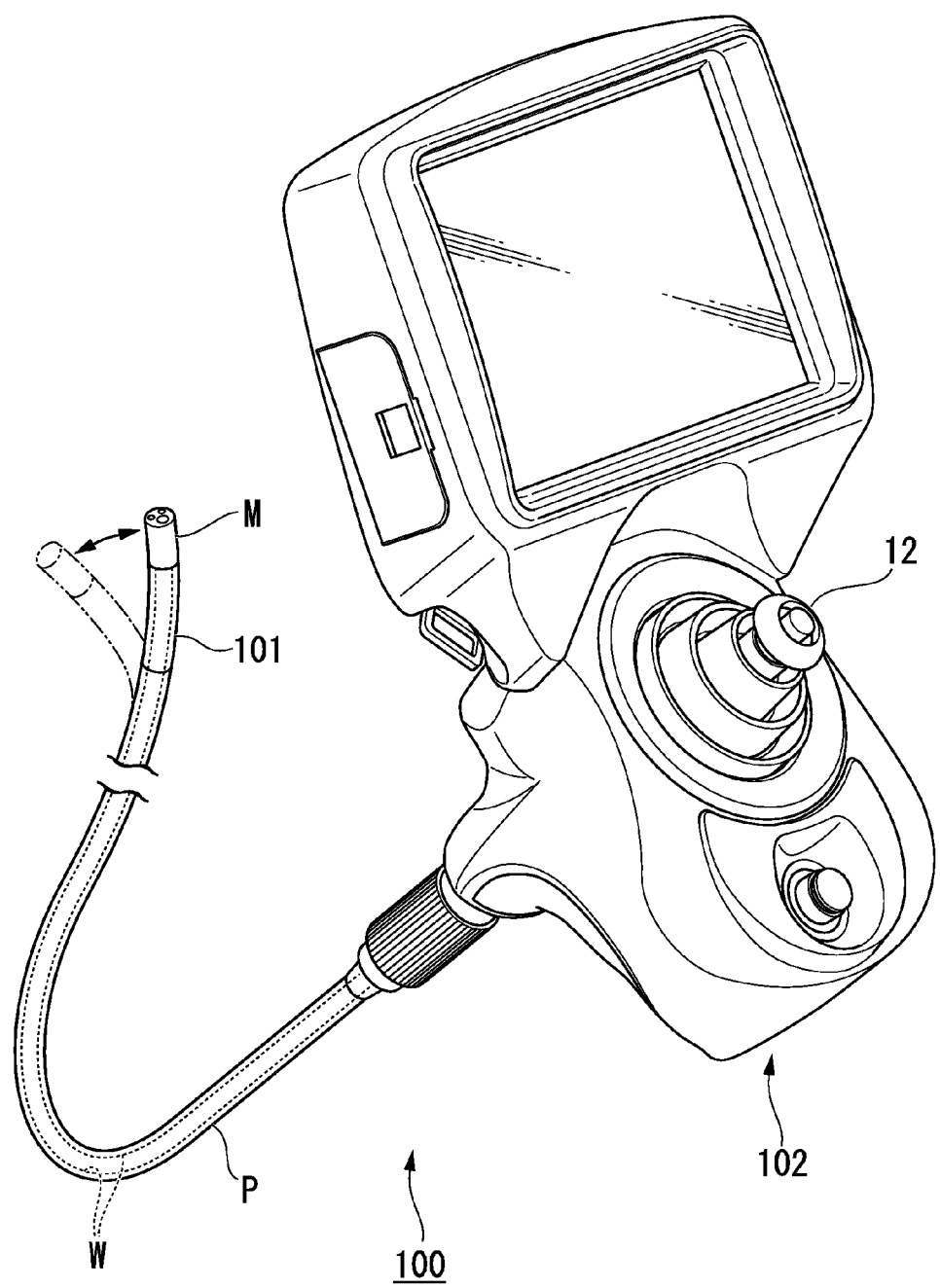
FIG. 1 is a perspective view showing an overall endoscopic apparatus related to a first embodiment of the present invention.

FIG. 1 is a view showing an overall endoscopic apparatus 100 of the present embodiment.

As shown in FIG. 1, the endoscopic apparatus 100 includes an insertion section P, an imaging mechanism M to that is located at a distal portion of the insertion section P, a bending section 101 (body to be operated) that is provided between the imaging mechanism M and the insertion section P and is bending-operated by a plurality of pulling wires W within the insertion section, and an operating section 102 that is provided at a proximal end portion of the insertion section P and operated by a user.

In order to bending-operate the bending section 101, a wire-pulling mechanism 1 that pulls the pulling wires W is provided inside the operating section 102. The endoscopic apparatus 100 related to the present embodiment is capable of bending and operating the bending section (body to be operated) 101 via the pulling wires W as the user performs the tilting operation of the operating section 102. This enables the endoscopic apparatus 100 to freely change the orientation of the imaging mechanism M located at the distal of the bending section 101.

Figure 2:
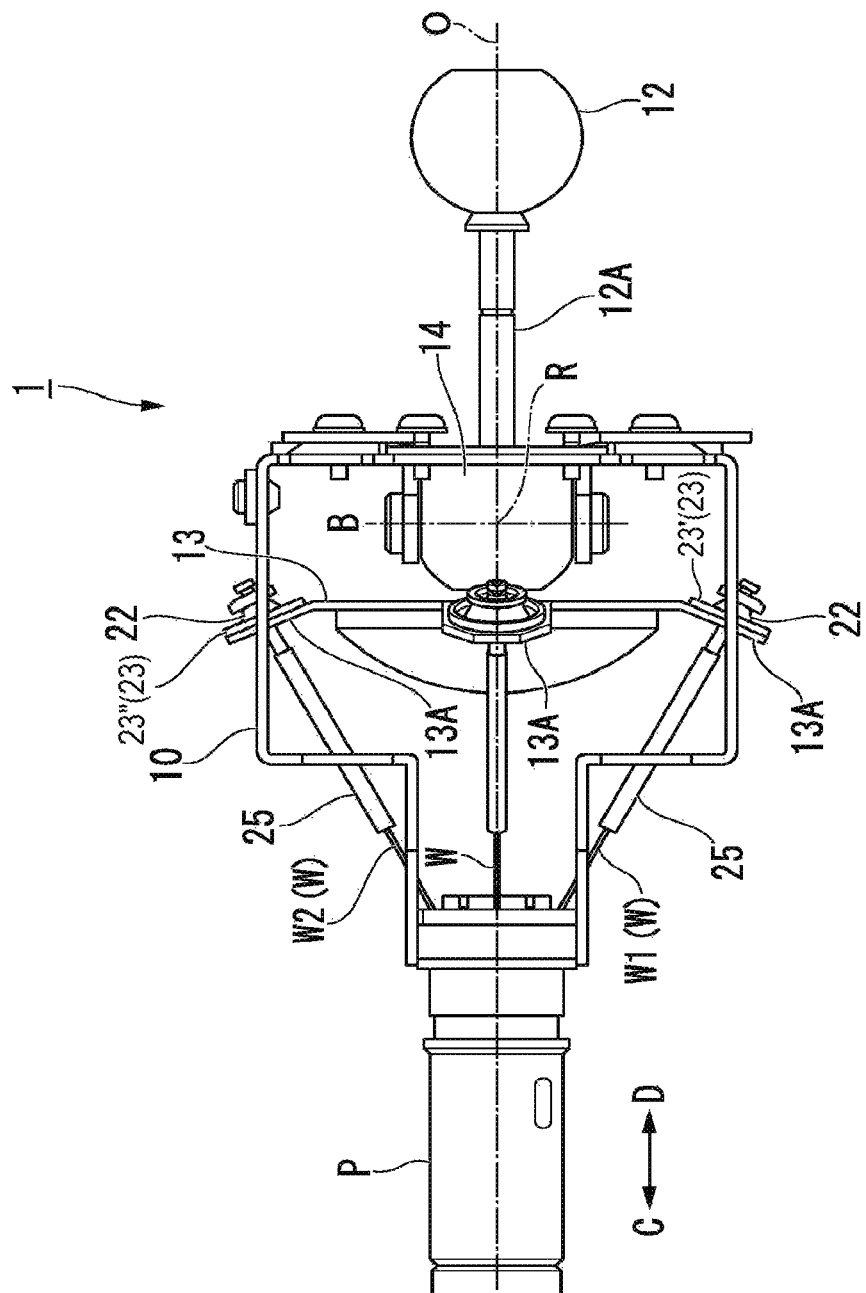
FIG. 2 is a schematic configuration view of a wire-pulling mechanism provided at the endoscopic apparatus.

FIG. 2 is a side view showing a schematic configuration of the wire-pulling mechanism provided at the endoscopic apparatus 100.

(First Pulling Wire and Second Pulling Wire)

One end (front end) of each of the plurality of pulling wires W is connected to the bending section 101 that is a body to be operated. Additionally, each of the plurality of pulling wires W has an engaged portion at the other end (rear end) extending rearward from one end. The engaged portion is connected to an engaging portion provided at a pulling arm to be described so as to be capable of engaging with or separating from the engaging portion.

Here, as shown in FIG. 2, one pulling wire W out of the pulling wires W is referred to a first pulling wire W1, and a pulling wire W arranged symmetrically with respect to the first pulling wire W1 is referred to as a second pulling wire W2.

(Operating Unit)

An operating unit pulls the first pulling wire W1 or the second pulling wire W2 by a tilting operation of a user. In the present embodiment, the operating unit is a joystick 12 that freely rocks and pivotally supports, and performs the tilting operation around a rocking point R by the user.

Figure 3:
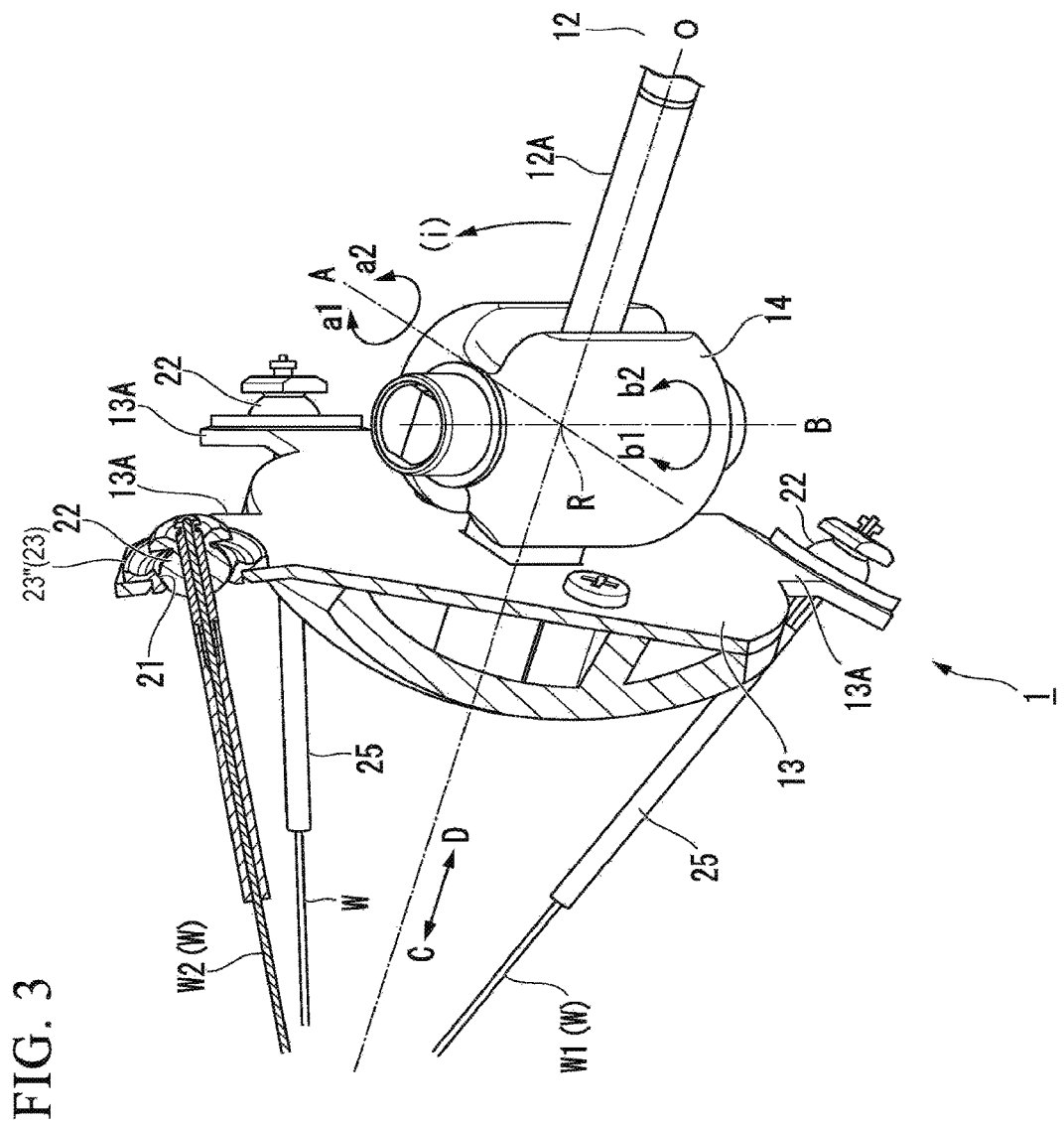
FIG. 3 is a perspective view when the wire-pulling mechanism is viewed obliquely from the rear side of the wire-pulling mechanism.

The joystick 12, as shown in FIG. 3, is supported by a bearing mechanism 14 supported by a frame 10 (refer to FIG. 2). The joystick 12 rocks by the bearing mechanism 14 so as to freely rock in the direction of arrow a1-a2 and in the direction of arrow b1-b2 around axes A and B that are in a positional relationship of passing through the rocking point R and being orthogonal to each other.

(Pulling Arm)

The pulling arm 13 is located on the front end of an operating shaft 12A of the joystick 12. The pulling arm 13 is provided with four protruding portions 13A that extend in a direction orthogonal to the central axis of the operating shaft 12A. The pulling wires W are connected to protruding ends (hereinafter may referred to as "outward portions") of the respective protruding portions 13A so as to be capable of engaging with or separating from the protruding ends.

The protruding ends (hereinafter may be referred to as "outward portions") of the respective protruding portions 13A of the pulling arm 13 are provided with engaging portions that are engageable with or separable from the engaged portions of the pulling wires W. The engaging portion moves along a predetermined movement track by a turning motion accompanying the tilting operation of the operating unit.

Additionally, the pulling arm 13 is formed in the shape of a disk as a whole. Four protruding portions 13A provided at the pulling arm 13 are provided at intervals of 90° at positions corresponding to the axes A and B.

Hereinafter, the characterizing portions of the present embodiment will be described in detail with reference to the drawings.

In a neutral state of the operating unit shown in FIG. 2, one pulling wire W out of the pulling wires W is referred to the first pulling wire W1, and the pulling wire W arranged symmetrically with respect to the first pulling wire W1 is referred to as the second pulling wire W2. Each of the first pulling wire W1 and the second pulling wire W2 includes an engaged portion (alternately referred to as a regulating member) 22, and each of the protruding ends of the protruding portions 13A of the respective pulling arms 13 includes an engaging portion (alternately referred to as a catcher) 23. In particular, the engaging portion 23 that is engageable with or separable from the engaged portion (regulating member) 22 of the first pulling wire W1 is referred to as a first engaging portion 23', and the engaging portion 23 that is engageable with or separable from the engaged portion (regulating member) of the second pulling wire W2 is referred to as a second engaging portion 23".

Figure 4:
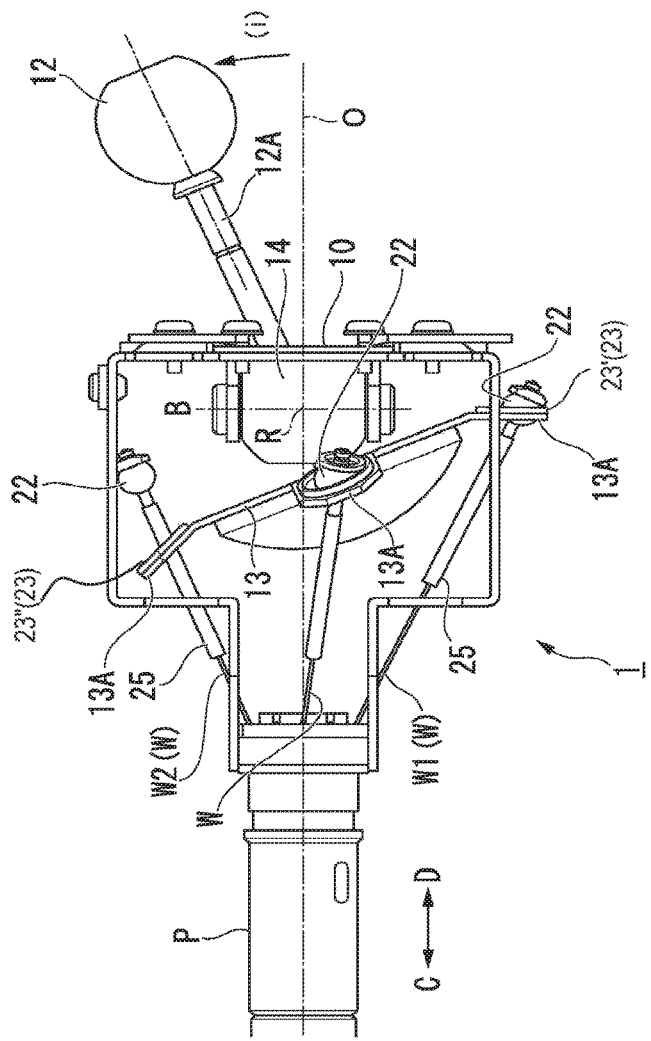
FIG. 4 is a schematic configuration view when the tilting operation of the wire-pulling mechanism is performed.

When shifting from the neutral state of the operating unit shown in FIG. 2 to a tilting state of the operating unit shown in FIG. 4 is made by the turning motion accompanying the tilting operation of the operating unit, the first engaging portion and the second engaging portion produce the following operations, respectively.

Figure 5:
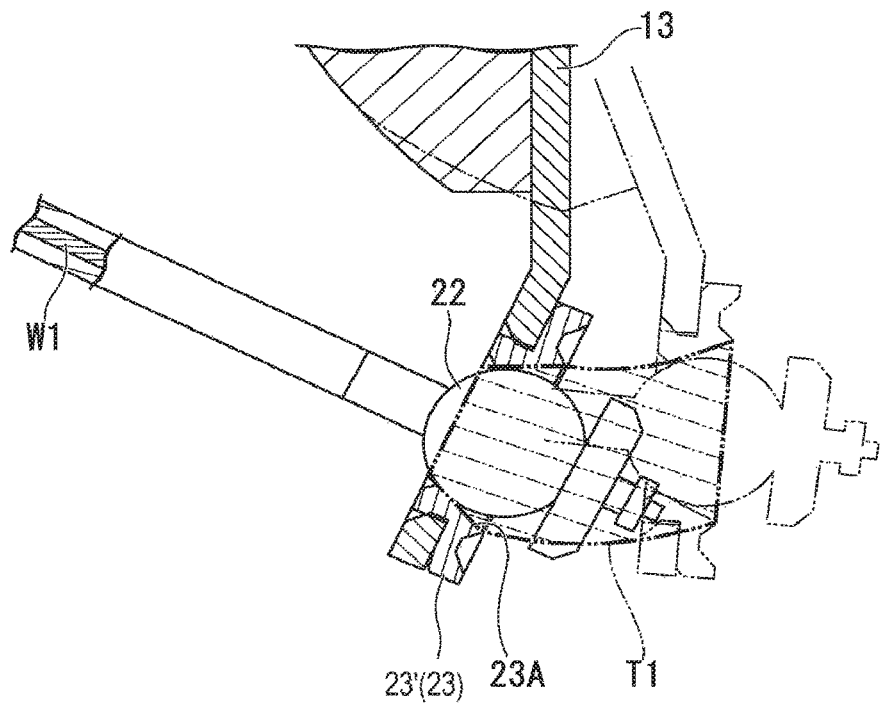
FIG. 5 is a view showing the movement track of a first engaging portion when the first engaging portion is moved rearward in the wire-pulling mechanism.
Figure 6:
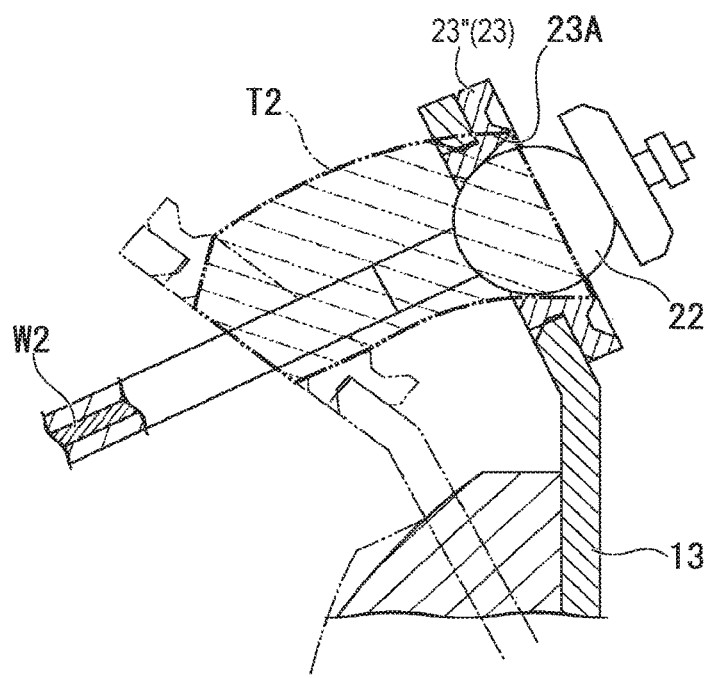
FIG. 6 is a view showing the movement track of a second engaging portion when the second engaging portion is moved forward in the wire-pulling mechanism.

That is, as shown in FIG. 5, the first engaging portion 23' pulls the first pulling wire W1 rearward along a first movement track T1. Additionally, as shown in FIG. 6, the second engaging portion 23" moves forward along a second movement track T2. Here, the first movement track T1 is a track that is formed by a tapered hole 23A of the first engaging portion 23' when the first engaging portion 23' moves rearward, in a state where the first engaging portion 23' and the engaged portion 22 of the first pulling wire W1. Additionally, the second movement track T2 is a track that is formed by a tapered hole 23A of the second engaging portion 23" when the second engaging portion 23" moves forward. That is, although the first movement track T1 and the second movement track T2 are shown as planes in FIGS. 5 and 6, the movement tracks are regions having spaces actually.

Figure 8:
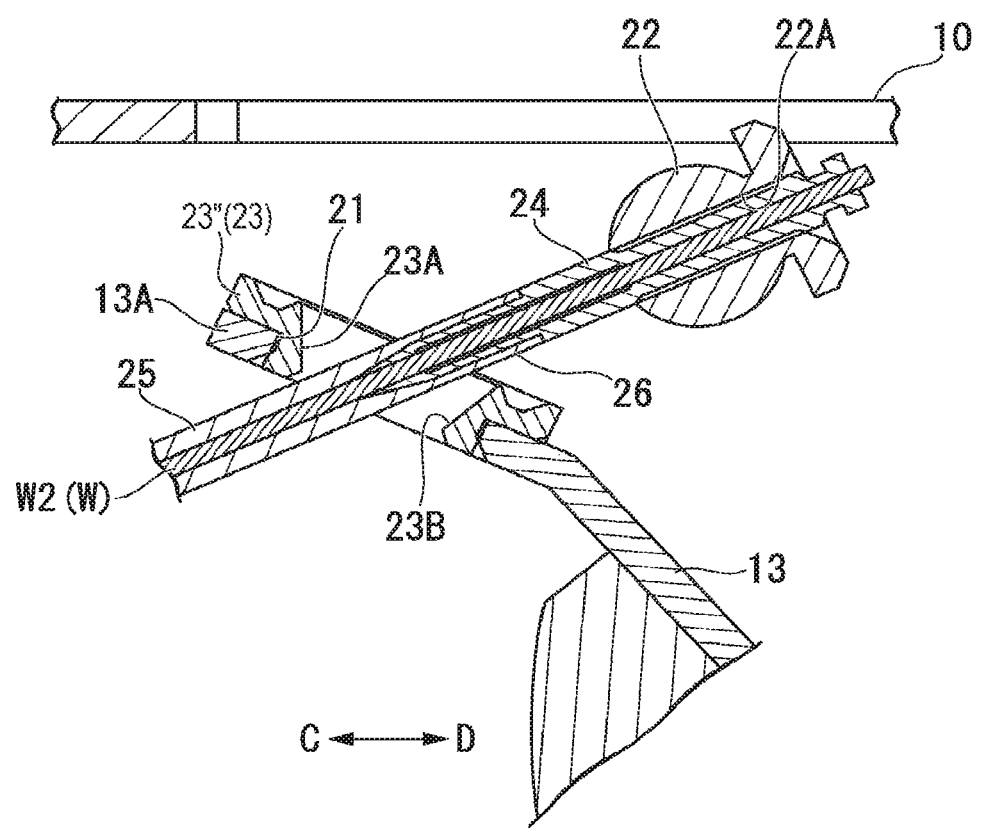
FIG. 8 is a view showing a state where the pulling wire is loosened in the wire-pulling mechanism.

As shown in FIGS. 2 and 8, the second engaging portion 23" is configured so that the position of the second engaging portion 23" in the longitudinal direction of the second pulling wire W2 is capable of being displaced closer to a front end (distal end) of the wire-pulling mechanism than the engaged portion 22 of the second pulling wire W2. In other words, the second engaging portion 23" is independently movable separately from the engaged portion 22, closer to the front end than the engaged portion 22 of the second pulling wire W2.

Additionally, the second engaging portion 23" is provided so as to allow insertion closer to the front end than the engaged portion 22 of the second pulling wire W2. The engaged portion 22 of the second pulling wire W2 and the second engaging portion 23" are configured so that the second engaging portion 23" is moved forward along the second movement track T2 with respect to the second pulling wire W2 and the engaged portion 22 of the second pulling wire W2 and the second engaging portion 23" are separated from each other.

In addition to the above configuration, in the neutral state of the operating unit, the second pulling wire W2 extends substantially linearly so as to enter the inside of the second movement track T2.

Since the wire-pulling mechanism of the present embodiment includes the above configuration, it is possible to suppress that the second pulling wire W2 and the second engaging portion 23" are brought into contact with each other with the separation operation of the second engaging portion 23". For this reason, when the body to be operated is bent and operated, the pulling wires (pulling members) can be kept from being loosened or curved, and degradation of the bending performance of the apparatus can be suppressed.

Next, the configuration in the present embodiment will be more specifically described.

As shown in FIG. 8, the second engaging portion 23" provided at the protruding portion 13A of the pulling arm 13 has a wire insertion region 21 that is movable relative to the second pulling wire W2.

The catcher 23 that has the tapered hole 23A whose internal diameter increases toward the proximal end side of the pulling wire W is attached to the wire insertion region 21. The catcher 23 is a receiving member that receives a regulating member 22 to be described below and holds the regulating member 22. The outer shape of the regulating member 22 is formed so as to be larger than the wire insertion region 21.

The regulating member 22 is provided on the other end (back) side of the pulling wire W to function as the engaged portion. The regulating member 22 has a substantially spherical shape whose external diameter is larger than the minimum internal diameter of the tapered hole 23A of the catcher 23. When the protruding portion 13A of the pulling arm 13 moves to the rear side (toward the direction of arrow D), the regulating member 22 comes into contact with a tapered surface 23B of the tapered hole 23A and is moved with the rocking point R (refer to FIG. 4) as a center. The pulling wire W is pulled by a constant length in this way.

Figure 7:
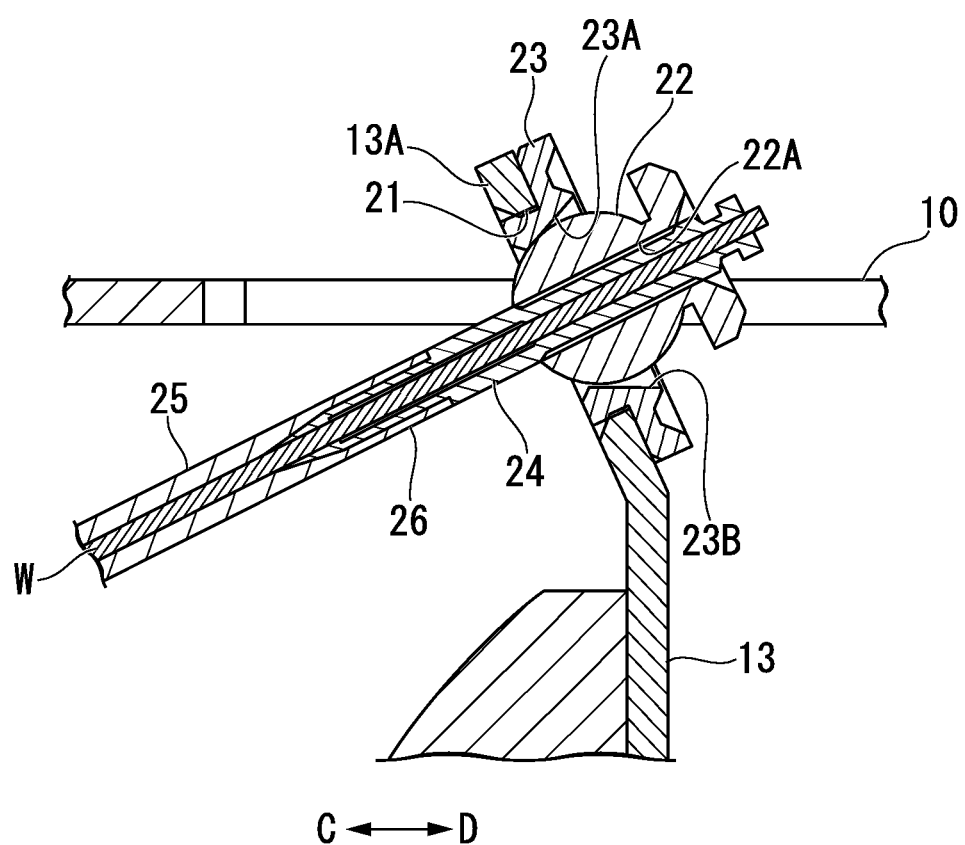
FIG. 7 is a view showing a state where a pulling wire is tensioned in the wire-pulling mechanism.

As shown in FIG. 7, the regulating member 22 is formed with a center hole 22A through which a proximal end portion of the pulling wire W is inserted. A fixing member 24 formed in the shape of a tube is provided between the proximal end portion of the pulling wire W and the regulating member 22. The fixing member 24 has a rear end portion fixed to the center hole 22A of the regulating member 22 by welding or screwing. Additionally, the pulling wire W is inserted through the inside of the fixing member 24, and the fixing member 24 and the pulling wire W are fixed together by soldering, welding, or bonding. Moreover, a guide pipe 25 installed at an outer peripheral portion of the pulling wire W is fitted to a front end portion of the fixing member 24. The external diameter of the fixing member 24 and the external diameter of the guide pipe 25 are made approximately equal to each other, and fitting portions 26 of the fixing member 24 and the guide pipe 25 are integrated by step portions formed so as to mesh with each other. In the fitting portions 26, the step portions of the fixing member 24 and the guide pipe 25 is fixed together by a well-known fixing method, such as bonding, welding, or brazing.

In the present embodiment, the regulating member 22 has a configuration in which the regulating member comes into linear contact with the tapered surface 23B of the tapered hole 23A.

Next, the operation of the wire-pulling mechanism 1 of the present embodiment will be described.

The wire-pulling mechanism 1 of the present embodiment is attached to the operating section 102 of the endoscopic apparatus 100, for example, as an operating mechanism for bending the bending section 101 of the endoscopic apparatus 100.

Although not shown in detail, in the present embodiment, the bending section 101 has the distals of the pulling wires W fixed thereto and is bent and operated by pulling the pulling wires W to the proximal end side. Additionally, a state where the bending section 101 is not bent is an initial state in the wire-pulling mechanism 1. In addition, in the initial state, the respective pulling arms 13 equally pulls all of the respective pulling wires W or do not pull any one of the respective pulling wires W.

In the initial state, the connecting positions between the proximal end portions of the respective pulling wires W and the respective pulling arms 13 are located ahead of the rocking point R.

In the wire-pulling mechanism 1, when the joystick 12 is tilted in the direction of arrow (i) from a reference axis O as shown in FIG. 4, the catcher 23 located at the protruding portion 13A of the pulling arm 13 moved to the rear side (toward the direction of arrow D) pulls the regulating member 22 in the same direction (toward the direction of arrow D) as shown in FIG. 7. As a result, the pulling wire W coupled to the regulating member 22 moves in the same direction (toward the direction of arrow D), and the bending section 101 of the distal of the pulling wire W is bent and operated by the pulling of the pulling wire W.

Simultaneously, when the joystick 12 is tilted from the reference axis O as shown in FIG. 4, the pulling arm 13 located on the opposite side across the rocking point R moves to the front end (toward the direction of arrow C). In the present embodiment, the pulling wire W is inserted through the tapered hole 23A of the catcher 23 located at the protruding portion 13A of the pulling am 13. Additionally, the pulling wire W is detachably supported by the catcher 23 via the fixing member 24 and the regulating member 22.

Accordingly, as shown in FIG. 8, when the pulling arm 13 has moved to the front end, the position of the proximal end portion of the pulling wire W is maintained at a position before the movement (initial state) of the pulling arm 13, and the pulling arm 13 moves to the front end (toward the direction of arrow C) relative to the pulling wire W. Additionally, since the protruding portion 13A of the pulling am 13 is moved so as to run substantially along the direction of the central axis of the pulling wire W, the pulling wire W can be kept from being forcedly bent or moved by the pulling arm 13.

By moving the pulling arm 13 to the front end (toward the direction of arrow C) relative to the pulling wire W, deflection of the pulling wire W connected to the pulling arm 13 can be suppressed. Additionally, when the bending rigidity of the pulling wire W is small and is easily deflected, rigidity is added to about the fixing member 24 of the pulling wire W with a guide pipe 25. This enables buckling at the time of attachment and detachment of the pulling wire W to be suppressed by the guide pipe 25.

In the above wire-pulling mechanism 1, when the joystick 12 is tilted from the reference axis O in this way, the rearward movement of the proximal end portion of the pulling wire W relative to the pulling arm 13 is allowed in a supporting place (the tapered hole 23A of the catcher 23 in the present embodiment) where the pulling wire W (the pulling wire W located opposite to the pulled pulling wire W across the rocking point R) on a loosening side (corresponding to a pulling side and where a pulling force is released) is supported by the pulling arm 13. At this time, the proximal end portion of the pulling wire W on the loosening side is separated from the pulling arm 13 by the wire-pulling mechanism 1 at a position (a position closer to the front end than the engaged portion 22 of the second pulling wire W2 of the second engaging portion 23") where the pulling force is released. This enables the pulling wire W to be deflected even if the joystick 12 is tilted from the reference axis O. Additionally, in the wire-pulling mechanism 1, the proximal end portion of the pulling wire W may be allowed to move to the rear side relative to the pulling arm 13 along the longitudinal direction of the pulling wire W.

In addition, if the bending section 101 is bent, the pulling wire W located outside the bending of the bending section 101 may be pulled to the distal side.

In this case, the proximal end of the pulling wire W on the loosening side may be moved to the distal side regardless of the position of the pulling arm 13. In the present embodiment, even in a case where the bending section 101 is bent, a force can be kept from being applied to the pulling wires W other than the first pulling wire W1 from the wire-pulling mechanism 1 because the pulling wires W other than the first pulling wire W1 pulled by the wire-pulling mechanism 1 is detachably supported by the catcher 23 via the fixing member 24 and the regulating member 22.

As described above, the wire-pulling mechanism 1 shown in the present embodiment is connected to the proximal end portions of the pulling wires W to selectively pull or loose the pulling wires W. Moreover, when the joystick 12 is tilted, the wire-pulling mechanism 1 allows the proximal end portion of the pulling wire W on the loosening side to relatively move to the rear side in the place where the pulling wire W is supported by the pulling arm 13. Accordingly, for example, when the operation of moving the pulling wires W is performed such that the bending section 101 is bent and operated, the pulling wires W (pulling members) can be kept from being loosened or curved.

Additionally, in the related art, if loosening or curvedness of the pulling wires is repeated, the pulling wires may break due to fatigue of the pulling wires or a curving tendency may be given to the pulling wires. In contrast, in the present embodiment, the proximal end portions of the pulling wires W are coupled to the pulling arm 13 via the regulating member 2 and the catcher 23. Thus, the pulling wires W are not forcedly bent by the pulling arm 13. As a result, even if the operation of the moving the pulling wires W, such as the bending operation of the bending section 101, is repeated, the bending performance of the apparatus, such as the endoscopic apparatus 100, does not deteriorate easily.

Additionally, in the wire-pulling mechanism 1, the regulating member 22 is formed in a substantially spherical shape, and is capable of being brought into line contact with the tapered surface 23B within the tapered hole 23A of the catcher 23 when a protruding portion 13A of the pulling arm 13 moves to the rear side (toward the direction of arrow D). Thus, the contact with the regulating member 22 and the catcher 23 can be stabilized, and the pulling wires W can be stably pulled.

In addition, in the above embodiment, the inside of the tapered hole 23A of the catcher 23 is formed as the tapered surface 23B and the tapered surface 23B and the spherical regulating member 22 are brought into line contact with each other. However, the inner surface of the catcher 23 may be formed as a spherical surface with a diameter slightly larger than the regulating member 22, and the regulating member 22 may be held in a stable state with respect to the catcher 23 by the contact between these spherical surfaces. That is, the inner surface of the catcher 23 may be formed in a shape resembling the external surface of the regulating member 22.

Additionally, in the present embodiment, in the above initial state where the bending section 101 is not bent, the connecting positions between the proximal end portions of the respective pulling wires W and the respective pulling arms 13 are located ahead of the rocking point R, and the respective pulling arms 13 rotate around the rocking point R. For this reason, the movement tracks of the proximal ends of the respective pulling wires W can be formed in the shape of a substantial straight line. As a result, when the respective pulling wires W are moved, excessive forces that bend the respective pulling wires W are not easily applied to the respective pulling wires W.

Second Embodiment

A second embodiment of the present invention will be described with reference to FIGS. 1 to 3, FIG. 9, and FIG. 10.

FIG. 1 is a view showing an overall endoscopic apparatus 100 of the present embodiment.

As shown in FIG. 1, the endoscopic apparatus 100 includes an insertion section P, an imaging mechanism M to that is located at a distal portion of the insertion section P, a bending section 101 (body to be operated) that is provided between the imaging mechanism M and the insertion section P and is bending-operated by a plurality of pulling wires W within the insertion section, and an operating section 102 that is provided at a proximal end portion of the insertion section P and operated by a user.

In order to bending-operate the bending section 101, a wire-pulling mechanism 2 that pulls the pulling wires W is provided inside the operating section 102. The endoscopic apparatus 100 related to the present embodiment is capable of bending and operating the bending section (body to be operated) 101 via the pulling wires W as the user performs the tilting operation of the operating section 102. This enables the endoscopic apparatus 100 to freely change the orientation of the imaging mechanism M located at the distal of the bending section 101.

FIG. 2 is a side view showing a schematic configuration of the wire-pulling mechanism 2 provided at the endoscopic apparatus 100.

(First Pulling Wire and Second Pulling Wire)

One end (front end) of each of the plurality of pulling wires W is connected to the bending section 101 that is a body to be operated. Additionally, each of the plurality of pulling wires W has an engaged portion at the other end (rear end) extending rearward from one end. The engaged portion is connected to an engaging portion provided at a pulling arm to be described so as to be capable of engaging with or separating from the engaging portion.

Here, as shown in FIG. 2, one pulling wire W out of the pulling wires W is referred to a first pulling wire W1, and a pulling wire W arranged symmetrically with respect to the first pulling wire W1 is referred to as a second pulling wire W2.

(Operating Unit)

An operating unit pulls the first pulling wire W1 or the second pulling wire W2 by a tilting operation of a user. In the present embodiment, the operating unit is a joystick 12 that freely rocks and pivotally supporting, and performs the tilting operation around a rocking point R by the user.

The joystick 12, as shown in FIG. 3, is supported by a bearing mechanism 14 supported by a frame 10 (refer to FIG. 2). The joystick 12 rocks by the bearing mechanism 14 so as to freely rock in the direction of arrow a1-a2 and in the direction of arrow b1-b2 around axes A and B that are in a positional relationship of passing through the rocking point R and being orthogonal to each other.

(Pulling Arm)

The pulling arm 13 is located on the front end of an operating shaft 12A of the joystick 12. The pulling arm 13 is provided with four protruding portions 13A that extend in a direction orthogonal to the central axis of the operating shaft 12A. The pulling wires W are connected to protruding ends (hereinafter may referred to as "outward portions") of the respective protruding portions 13A so as to be capable of engaging with or separating from the protruding ends.

The protruding ends (hereinafter may be referred to as "outward portions") of the protruding portions 13A of the pulling arm 13 are provided with engaging portions that are engageable with or separable from the engaged portions of the pulling wires W. The engaging portion moves along a predetermined movement track by a turning motion accompanying the tilting operation of the operating unit.

Additionally, the pulling arm 13 is formed in the shape of a disk as a whole. Four protruding portions 13A provided at the pulling arm 13 are provided at intervals of 90° at positions corresponding to the axes A and B.

Additionally, even in the second embodiment, similar to the first embodiment, the first engaging portion 23', as shown in FIG. 5, pulls the first pulling wire W1 rearward along a first movement track T1. Additionally, as shown in FIG. 6, the second engaging portion 23" moves forward along a second movement track T2.

Figure 9:
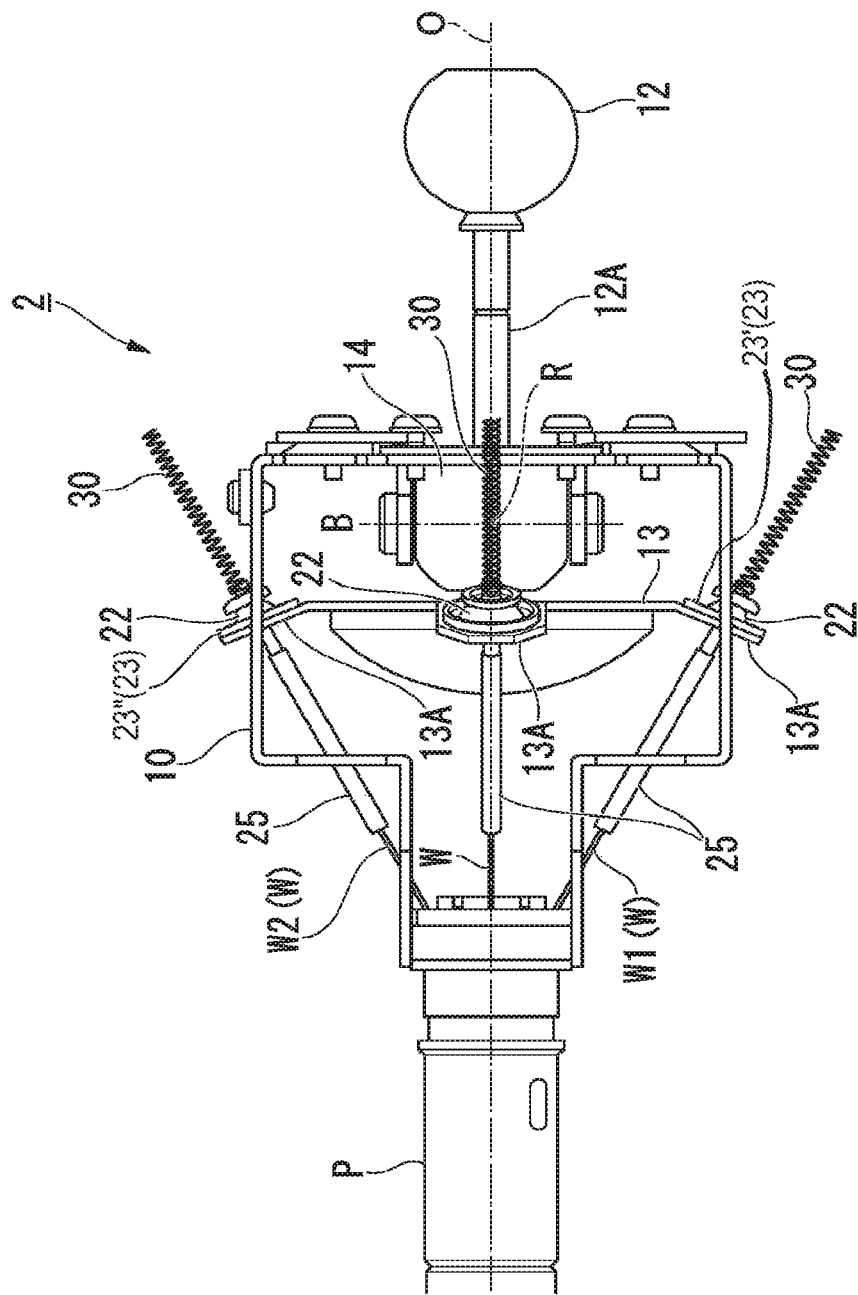
FIG. 9 is a schematic configuration view of a wire-pulling mechanism related to a second embodiment of the present invention.
Figure 10:
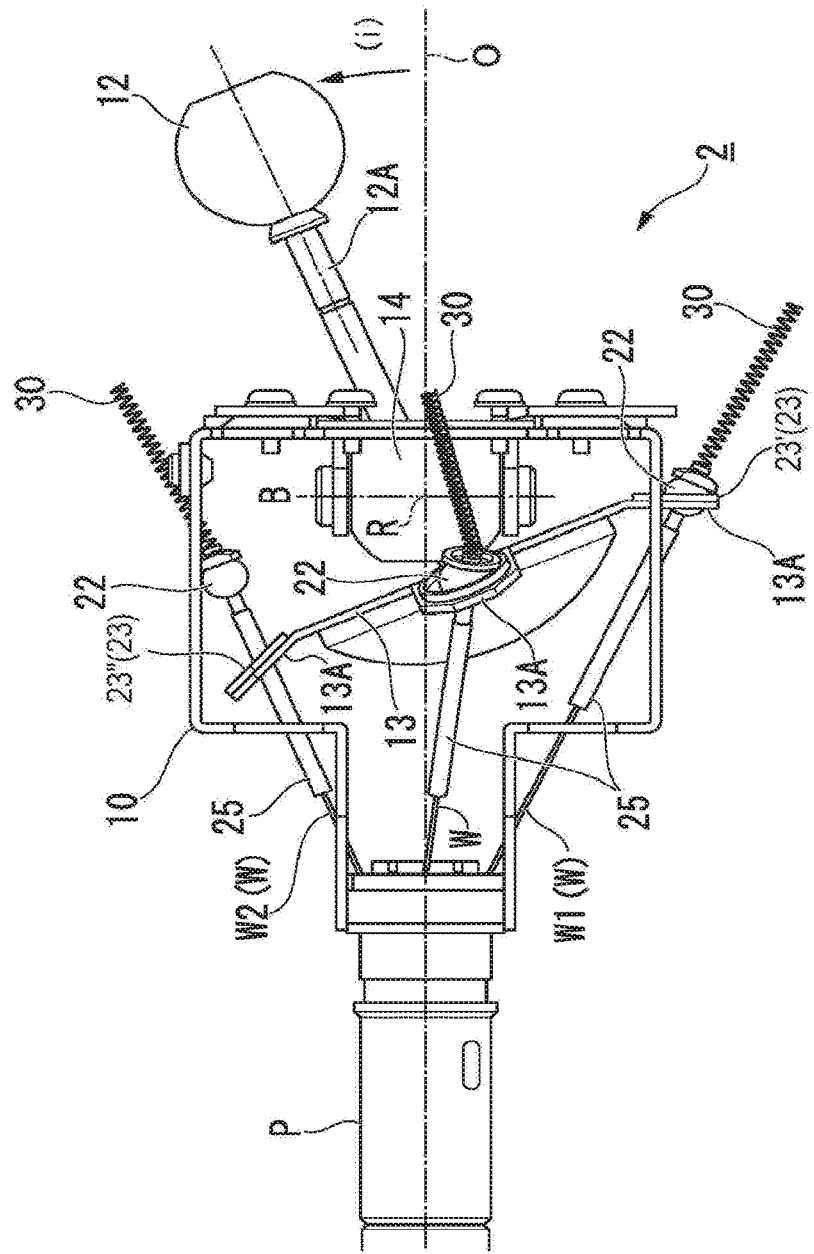
FIG. 10 is a schematic configuration view when the tilting operation of the wire-pulling mechanism is performed.
Figure 11:
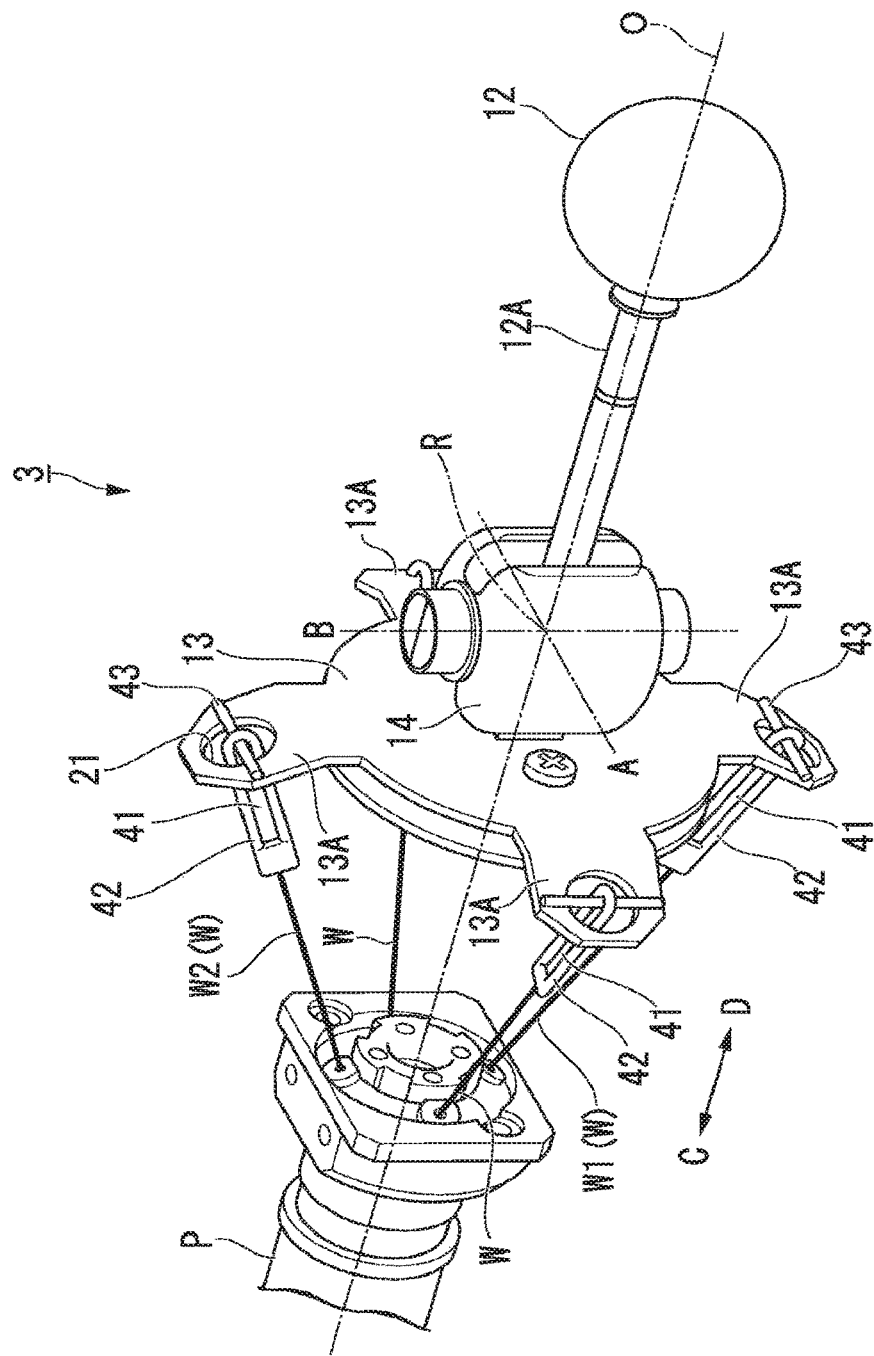
FIG. 11 is a schematic configuration view of a wire-pulling mechanism related to a third embodiment of the present invention.

The configuration of the wire-pulling mechanism 2 of this second embodiment is different from that of the wire-pulling mechanism 1 of the above-described first embodiment in that an auxiliary pulling member 30 is included as shown in FIGS. 9 and 10.

The auxiliary pulling member 30 is constituted by an elastic body, such as a compression spring or hard rubber.

Additionally, a front end portion (one end portion) of this auxiliary pulling member 30 is connected to the proximal end portion of the pulling wire W, and a rear end portion (other end portion) of the auxiliary pulling member 30 is supported by a supporting member (not shown). This supporting member may be the frame 10. Additionally, when the wire-pulling mechanism 2 of the present embodiment is included in the above-described endoscopic apparatus 100, the supporting member may be a sheathing case of the operating section 102. Additionally, the rear end portion of the auxiliary pulling member 30 may be supported by another member fixed to the frame 10 or the sheathing case.

The auxiliary pulling member 30 biases the proximal end of the pulling wire W to the rear end side of the wire-pulling mechanism 2. As a result, a constant tension (preload) is applied to the pulling wire W.

As shown in FIG. 10, when the user tilts the joystick 12 in the direction of arrow (i) and the pulling arm 13 located on the upper side (in the drawing) of the rocking point R moves to the front end (toward the direction of arrow C), the rear end portion of the pulling wire W protruding from the tapered hole 23A of the catcher 23 is supported by the supporting member via the auxiliary pulling member 30. This can keep the rear end portion of the pulling wire W protruding from the tapered hole 23A of the catcher 23 from rocking.

As described above, in the wire-pulling mechanism 2 shown in the present embodiment, when the pulling arm 13 is relatively moved to the front end (toward the direction of arrow C) along the pulling wire W as shown in FIG. 9 by the auxiliary pulling member 30 connected to the proximal end portion of the pulling wire W, the pulling wire W can be stabilized by suppressing deflection of the protruding pulling wire W. Additionally, the aforementioned process continuously generates a tension in the pulling wire W, and thus, a preload is stably generated.

In addition, in the present embodiment, the inside of the tapered hole 23A of the catcher 23 is formed as the tapered surface 23B and the tapered surface 23B and the spherical regulating member 22 are brought into line contact with each other. However, the inner surface of the catcher 23 may be formed as a spherical surface with a diameter slightly larger than the regulating member 22, and the regulating member 22 may be held in a stable state with respect to the catcher 23 by the contact between these spherical surfaces. That is, the inner surface of the catcher 23 may be formed in a shape resembling the external surface of the regulating member 22.

Additionally, in the present embodiment, in the above initial state where the bending section 101 is not bent, the connecting positions between the proximal end portions of the respective pulling wires W and the respective pulling arms 13 are located ahead of the rocking point R, and the respective pulling arms 13 rotate around the rocking point R. For this reason, the movement tracks of the proximal ends of the respective pulling wires W can be formed in the shape of a substantial straight line. As a result, when the respective pulling wires W are moved, the excessive forces that bend the respective pulling wires W are not easily applied to the pulling wires W.

Third Embodiment

A third embodiment of the present invention will be described with reference to FIGS. 1 to 3 and FIGS. 11 to 14. Here, in order to describe the overall configuration of the endoscopic apparatus 100, the description is made with reference to FIGS. 1 to 3. However, a wire-pulling mechanism 3 of the third embodiment differ in the wire-pulling mechanism 1 shown in FIGS. 1 and 2.

FIG. 1 is a view showing an overall endoscopic apparatus 100 of the present embodiment.

As shown in FIG. 1, the endoscopic apparatus 100 includes an insertion section P, an imaging mechanism M to that is located at a distal portion of the insertion section P, a bending section 101 (body to be operated) that is provided between the imaging mechanism M and the insertion section P and is bending-operated by a plurality of pulling wires W within the insertion section, and an operating section 102 that is provided at a proximal end portion of the insertion section P and operated by a user.

In order to bending-operate the bending section 101, a wire-pulling mechanism 3 that pulls the pulling wires W is provided inside the operating section 102. The wire-pulling mechanism 3 will be described below in detail with reference to FIG. 11. The endoscopic apparatus 100 related to the present embodiment is capable of bending and operating the bending section (body to be operated) 101 via the pulling wires W as the user performs the tilting operation of the operating section 102. This enables the endoscopic apparatus 100 to freely change the orientation of the imaging mechanism M located at the distal of the bending section 101.

FIG. 2 is a side view showing a schematic configuration of the wire-pulling mechanism 3 provided at the endoscopic apparatus 100.

(First Pulling Wire and Second Pulling Wire)

One end (front end) of each of the plurality of pulling wires W is connected to the bending section 101 that is a body to be operated. Additionally, each of the plurality of pulling wires W has an engaged portion at the other end (front end) extending rearward from one end. The engaged portion is connected to an engaging portion provided at a pulling arm to be described so as to be capable of engaging with or separating from the engaging portion.

Here, as shown in FIG. 2, one pulling wire W out of the pulling wires W is referred to a first pulling wire W1, and a pulling wire W arranged symmetrically with respect to the first pulling wire W1 is referred to as a second pulling wire W2.

(Operating Unit)

An operating unit pulls the first pulling wire W1 or the second pulling wire W2 by a tilting operation of a user. In the present embodiment, the operating unit is a joystick 12 that freely rocks and pivotally supported, and performs the tilting operation around a rocking point R by the user.

The joystick 12, as shown in FIG. 3, is supported by a bearing mechanism 14 supported by a frame 10 (refer to FIG. 2). The joystick 12 rocks by the bearing mechanism 14 so as to freely rock in the direction of arrow a1-a2 and in the direction of arrow b1-b2 around axes A and B that are in a positional relationship of passing through the rocking point R and being orthogonal to each other.

(Pulling Arm)

The pulling arm 13 is located on the front end of an operating shaft 12A of the joystick 12. The pulling arm 13 is provided with four protruding portions 13A that extend in a direction orthogonal to the central axis of the operating shaft 12A. The pulling wires W are connected to protruding ends (hereinafter may referred to as "outward portions") of the respective protruding portions 13A so as to be capable of engaging with or separating from the protruding ends.

The protruding end (hereinafter may be referred to as an "outward portion") of each protruding portion 13A of the pulling arm 13 is provided with an engaging portion that is engageable with or separable from the engaged portion of the pulling wire W. The engaging portion moves along a predetermined movement track by a turning motion accompanying the tilting operation of the operating unit.

Additionally, the pulling arm 13 is formed in the shape of a disk as a whole. Four protruding portions 13A provided at the pulling arm 13 are provided at intervals of 90° at positions corresponding to the axes A and B.

The configuration of the wire-pulling mechanism 3 of this third embodiment, as shown in FIGS. 11 to 14, is different from the configuration of the wire-pulling mechanism 1 described in the first embodiment.

The wire-pulling mechanism 3 has a connecting fitting (a connecting member or an engaged portion) 42 that is attached to the proximal end portion of the pulling wire W and has an elongated hole (engaging portion insertion region) 41, and a fixing bar (a contacting member or a second engaging portion) 43 that is installed at the protruding portion 13A of the pulling arm 13, is inserted through the elongated hole 41 of the connecting fitting 42, and is made movable along the elongated hole 41.

The characterizing portions of the present embodiment will be described below with reference to the drawings.

Figure 13:
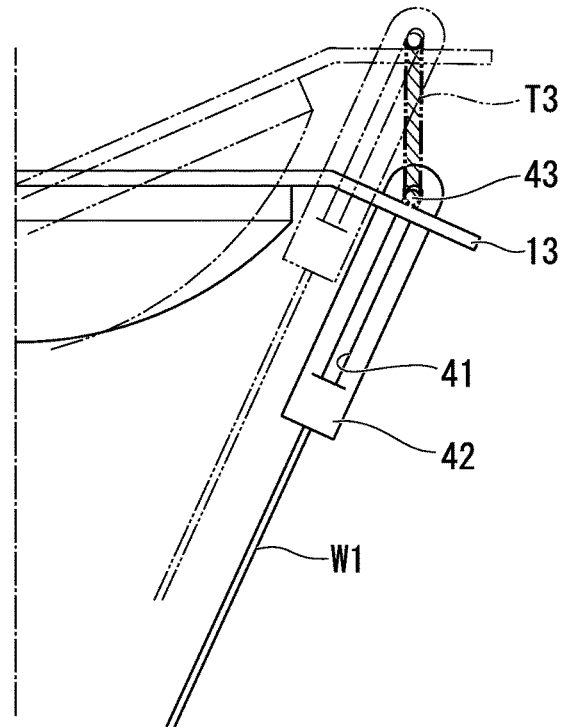
FIG. 13 is a view showing the movement track of a first engaging portion when the first engaging portion is moved rearward in the wire-pulling mechanism.

As shown in FIG. 13, the fixing bar 43 pulls the first pulling wire W1 rearward along a first movement track T3.

Figure 14:
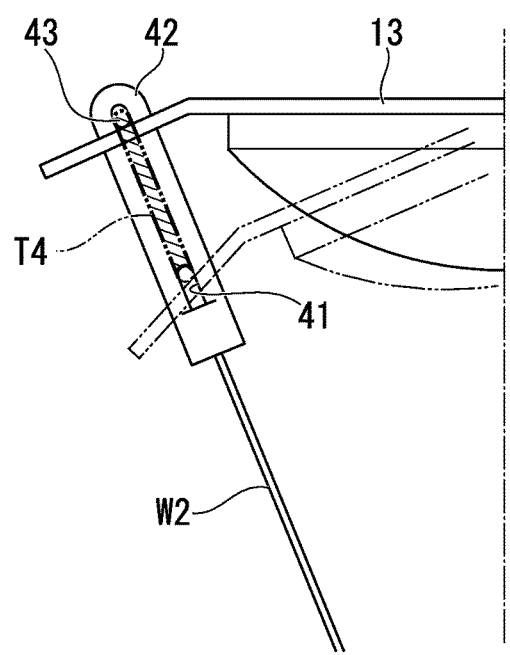
FIG. 14 is a view showing the movement track of a second engaging portion when the second engaging portion is moved forward in the wire-pulling mechanism.

Additionally, as shown in FIG. 14, the second engaging portion 43 moves forward along a second movement track T4. Here, the first movement track T3 is a track that is formed by the fixing bar 43 when the fixing bar 43 moves rearward in a state where the fixing bar 43 and the connecting member 42 of the first pulling wire W1 engage each other. Additionally, the second movement track T4 is a track that is formed by the fixing bar 43 when the fixing bar 43 moves forward. That is, although the first movement track T3 and the second movement track T4 are shown as planes in FIGS. 13 and 14, the movement tracks are regions having spaces in practice. The fixing bar 43 is configured so that the position of the fixing bar 43 in the longitudinal direction of the second pulling wire W2 is displaceable closer to the front end than the connecting member 42 of the second pulling wire W2. In other words, the fixing bar 43 is independently movable separately from the connecting member 42.

Next, the present embodiment will be more specifically described.

The fixing bar 43 is arranged so as to traverse a central portion of the elongated hole (engaging portion insertion region) 41 formed in the protruding portion 13A of the pulling arm 13. The cross-section of the fixing bar 43 is formed in a circular shape, the fixing bar 43 comes into line contact with an inner surface of the elongated hole 41 formed in the connecting fitting 42, and the contact resistance of the fixing bar with the connecting fitting 42 is suppressed so as to be low.

Figure 12:
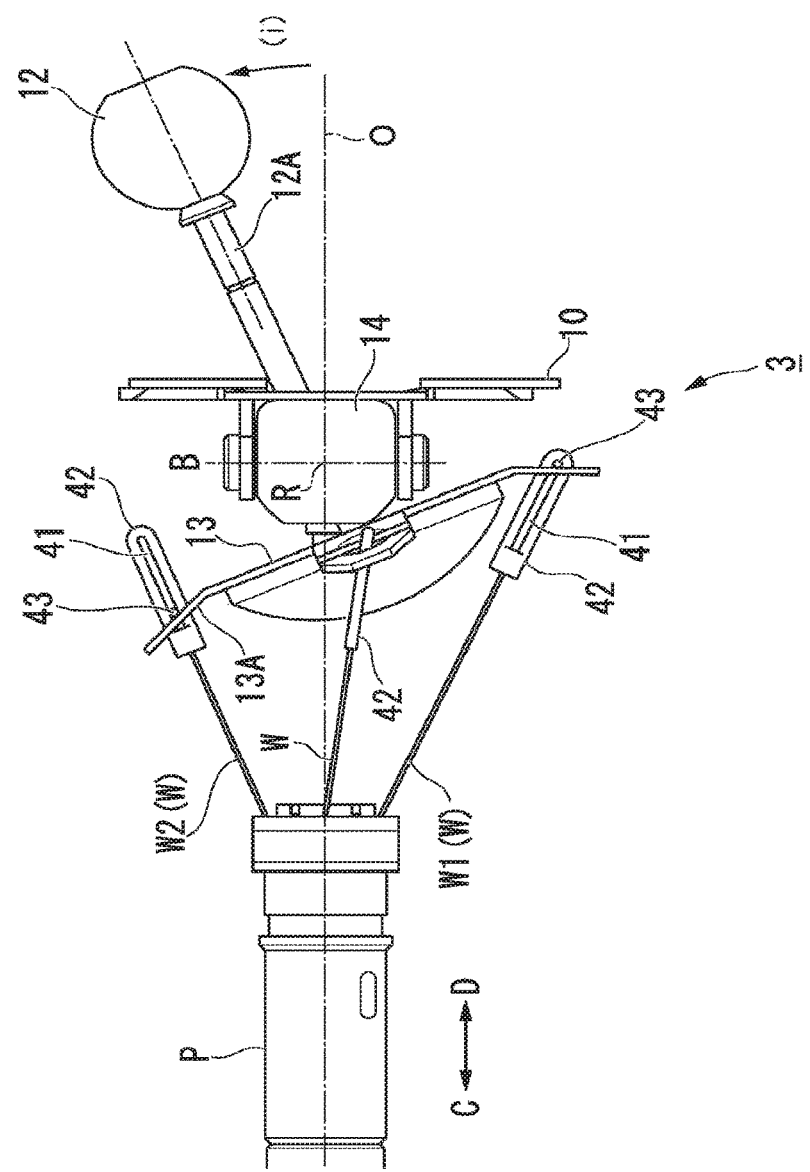
FIG. 12 is a schematic configuration view when the tilting operation of the wire-pulling mechanism is performed.

In the present embodiment, as shown in FIG. 12, when the joystick 12 is tilted in the direction of arrow (i) and the pulling arm 13 located on the upper side (in the drawing) of the rocking point R moves to the front end (toward the direction of arrow C), the fixing bar 43 installed in the elongated hole (engaging portion insertion region) 41 of the pulling arm 13 similarly moves to the front end (toward the direction of arrow C) within the elongated hole 41 of the connecting fitting 42. At this time, the connecting fitting 42 itself does not move to the front end. That is, the pulling wire W fixed at the connecting fitting 42 does not move to the front end either. As a result, deflection of the pulling wire W caused by the movement of the pulling arm 13 to the front end (toward the direction of arrow C) with respect to the pulling wire W can be suppressed by the connecting member 42 and the fixing bar 43.

As described above, when the pulling arm 13 is relatively moved to the front end (toward the direction of arrow C) along the pulling wire W as shown in FIG. 12 by the connecting member 42 and the fixing bar 43 installed between the pulling wire W and the pulling arm 13, deflection of the pulling wire W can be suppressed. As a result, the pulling wire W can be stabilized in the wire-pulling mechanism 3 shown in the present embodiment. Additionally, in the wire-pulling mechanism 3, as the fixing bar 43 on the pulling arm 13 side is passed through the elongated hole 41 of the connecting fitting 42, twisting of the pulling wire W can be suppressed together with the connecting fitting 42, and a stable pulling operable of the body to be operated can be performed.

In addition, the configuration of the wire-pulling mechanism 3 of the present embodiment may include the auxiliary pulling member 30, similar to the configuration of the wire-pulling mechanism 2 of the second embodiment.

The auxiliary pulling member 30 is constituted by an elastic body, such as a compression spring or hard rubber.

Additionally, a front end portion (one end portion) of this auxiliary pulling member 30 is connected to the proximal end portion of the connecting fitting 42, and a rear end portion (other end portion) of the auxiliary pulling member 30 is supported by a supporting member (not shown). This supporting member may be the frame 10. Additionally, when the wire-pulling mechanism 2 of the present embodiment is included in the above-described endoscopic apparatus 100, the supporting member may be a sheathing case of the operating section 102. Additionally, the rear end portion of the auxiliary pulling member 30 may be supported by another member fixed to the frame 10 or the sheathing case.

The auxiliary pulling member 30 biases the proximal end of the connecting fitting 42 to the rear end side of the wire-pulling mechanism 2. As a result, a constant tension (preload) is applied to the pulling wire W.

As shown in FIG. 12, when the user tilts the joystick 12 in the direction of arrow (i) and the pulling arm 13 located on the upper side (in the drawing) of the rocking point R moves to the front end (toward the direction of arrow C), the rear end portion of the connecting fitting 42 is supported by the supporting member via the auxiliary pulling member 30 (not shown). This can keep the connecting fitting 42 from rocking.

As described above, when the pulling am 13 is relatively moved to the front end (toward the direction of arrow C) along the pulling wire W by the auxiliary pulling member 30 connected to the proximal end portion of the connecting fitting 42, the pulling wire W can be stabilized by suppressing deflection of the protruding pulling wire W. Additionally, the aforementioned process continuously generates a tension in the pulling wire W, and thus, a preload is stably generated.

While preferred embodiments of the present invention have been described, the present invention is not limited to the embodiments. Additions, omissions, substitutions, and other variations may be made to the present invention without departing from the spirit and scope of the present invention. The present invention is not to be considered as being limited by the foregoing description, and is limited only by the scope of the appended claims.

The invention claimed is:

1. A wire-pulling mechanism comprising:
a first pulling wire and a second pulling wire a distal end of each of which is connected to a body to be operated, the body being disposed at a distal end portion of each of the first pulling wire and the second pulling wire, and each of the first pulling wire and the second pulling wire having an engaged portion at a proximal end thereof extending rearward from the distal end;
an operating unit pulling the first pulling wire or the second pulling wire by a tilting operation performed by a user; and
a pulling arm having a first engaging portion that is directly engageable with and separable from the engaged portion of the first pulling wire and a second engaging portion that is directly engageable with and separable from the engaged portion of the second pulling wire, the first engaging portion pulling the first pulling wire along a first movement track when the first engaging portion moves rearward in a state where the first engaging portion and the engaged portion of the first pulling wire engage each other, and the second engaging portion moving along a second movement track when the second engaging portion moves toward a distal end of the mechanism, the pulling of the first engaging portion and the moving of the second engaging portion being caused by a turning motion accompanying the tilting operation of the operating unit,
wherein the second engaging portion is configured so that a position of the second engaging portion in a longitudinal direction of the second pulling wire is capable of being displaced closer to the distal end of the mechanism than the engaged portion of the second pulling wire, wherein the second pulling wire extends in a straight line within the second movement track along an entirety of the second movement track, in a neutral state of the operating unit, and wherein the pulling arm is configured such that a movement amount of the second movement track is larger than an engagement amount by which the second engaging portion is directly engaged with the engaged portion of the second pulling wire.

2. The wire-pulling mechanism according to claim 1, wherein the second engaging portion has a wire insertion region that is movable relative to the second pulling wire.

3. The wire-pulling mechanism according to claim 1, wherein the engaged portion of the second pulling wire has an engaging portion insertion region where the second engaging portion is movable in an extending direction of the second pulling wire relative to the second pulling wire, and wherein the second engaging portion is a contacting member that comes into contact with a rear end portion of the engaging portion insertion region.

4. The pulling mechanism according to claim 3, wherein the engaging portion insertion region is an elongated hole that is formed toward the longitudinal direction of the second pulling wire, wherein the engaged portion of the second pulling wire is a connecting member having the elongated hole, and wherein the contacting member is inserted through the elongated hole of the connecting member and is provided so as to be movable along the elongated hole.

5. The wire-pulling mechanism according to claim 1, wherein an auxiliary pulling member made of an elastic body is installed on the other end side of the second pulling wire, wherein a front end side of the auxiliary pulling member is coupled to the other end side of the second pulling wire, wherein a rear end side of the auxiliary pulling member is supported by a predetermined supporting member, and wherein the auxiliary pulling member biases the second pulling wire rearward.

6. The wire-pulling mechanism according to claim 2, wherein the engaged portion of the second pulling wire is a regulating member an outer shape of which is formed larger than an outer shape of the wire insertion region.

7. The wire-pulling mechanism according to claim 6, wherein each of the first engaging portion and the second engaging portion is a receiving member formed with a circular tapered hole having a taper shape such that a diameter of the taper shape increases gradually toward a proximal end side thereof.

8. The wire-pulling mechanism according to claim 7, wherein the receiving member is formed at the wire insertion region.

9. The wire-pulling mechanism according to claim 8, wherein the regulating member has a substantially spherical shape a diameter of which is larger than a minimum internal diameter of the tapered hole of the receiving member.

10. The wire-pulling mechanism according to claim 8, wherein the regulating member comes into contact with a tapered surface of the tapered hole in the neutral state of the operating unit.

11. An endoscopic apparatus comprising:
a first pulling wire and a second pulling wire a distal end of each of which is connected to a distal end side of an insertion section, and a proximal end of each of which is arranged within an operating section, each of the first pulling wire and the second pulling wire having an engaged portion provided at the proximal end thereof;

an operating unit pulling the first pulling wire or the second pulling wire by a tilting operation performed by a user; and a pulling arm having a first engaging portion that is directly engageable with and separable from the engaged portion of the first pulling wire and a second engaging portion that is directly engageable with and separable from the engaged portion of the second pulling wire, the first engaging portion pulling the first pulling wire along a first movement track when the first engaging portion moves rearward in a state where the first engaging portion and the engaged portion of the first pulling wire engage each other, and the second engaging portion moving along a second movement track when the second engaging portion moves toward a distal end of the mechanism, the pulling of the first engaging portion and the moving of the second engaging portion being caused by a turning motion accompanying the tilting operation of the operating unit, wherein the second engaging portion is configured so that a position of the second engaging portion in a longitudinal direction of the second pulling wire is capable of being displaced closer to the distal end of the mechanism than the engaged portion of the second pulling wire, wherein the second pulling wire extends in a straight line within the second movement track along an entirety of the second movement track, in a neutral state of the operating unit, and wherein the pulling arm is configured such that a movement amount of the second movement track is larger than an engagement amount by which the second engaging portion is directly engaged with the engaged portion of the second pulling wire.

12. The endoscopic apparatus according to claim 11, wherein the second engaging portion has a wire insertion region that is movable relative to the second pulling wire.

13. The endoscopic apparatus according to claim 12, wherein the engaged portion of the second pulling wire is a regulating member an outer shape of which is formed larger than an outer shape of the wire insertion region.

14. The endoscopic apparatus according to claim 13, wherein each of the first engaging portion and the second engaging portion is a receiving member formed with a circular tapered hole having a taper shape such that a diameter of the taper shape increases gradually toward a proximal end side thereof.

15. The endoscopic apparatus according to claim 14, wherein the receiving member is formed at the wire insertion region.

16. The endoscopic apparatus according to claim 15, wherein the regulating member has a substantially spherical shape a diameter of which is larger than a minimum internal diameter of the tapered hole of the receiving member.

17. The endoscopic apparatus according to claim 15, wherein the regulating member comes into contact with a tapered surface of the tapered hole in the neutral state of the operating unit.

* * * * *